(12) United States Patent
Beltran et al.

(10) Patent No.: US 7,196,117 B2
(45) Date of Patent: Mar. 27, 2007

(54) USE OF CATIONIC SURFACTANT AS ACTIVITY ENHANCER IN DEODORANTS AND ORAL CARE

(75) Inventors: Joan Baptista Urgell Beltran, Barcelona (ES); Joan Seguer Bonaventura, L'Hospitalet de Llobregat/Barcelona (ES)

(73) Assignee: Laboratorios Miret, S.A., Barcelona (ES)

( * ) Notice: Subject to any disclaimer, the term of this patent is extended or adjusted under 35 U.S.C. 154(b) by 24 days.

(21) Appl. No.: 10/494,926

(22) PCT Filed: Nov. 25, 2001

(86) PCT No.: PCT/EP01/13221

§ 371 (c)(1),
(2), (4) Date: May 7, 2004

(87) PCT Pub. No.: WO03/043593

PCT Pub. Date: May 30, 2003

(65) Prior Publication Data

US 2004/0254232 A1 Dec. 16, 2004

(51) Int. Cl.
*A61K 31/22* (2006.01)
*A61K 31/415* (2006.01)
(52) U.S. Cl. ............ 514/551; 514/396; 514/549; 548/338.1; 560/169
(58) Field of Classification Search ............ None
See application file for complete search history.

(56) References Cited

FOREIGN PATENT DOCUMENTS

| EP | 0 485 616 | 5/1992 |
|---|---|---|
| EP | 0 749 960 | 12/1996 |
| FR | 2 143 557 | 2/1973 |

OTHER PUBLICATIONS

Database CA Online Chemical Abstract Services. "Anti-microbial cosmetics having low irritability." JP 10045557 (1998).
Database CA Online Chemical Abstract Services. "Antibacterial, low-irritation cosmetics." JP 09255518 (1997).

*Primary Examiner*—Brian Davis
(74) *Attorney, Agent, or Firm*—Renner, Otto, Boisselle Sklar, LLP

(57) ABSTRACT

Antimicrobial system which comprises a cationic surfactant, derived from the condensation of fatty acids and esterified dibasic amino acids, according to the following formula (I), where: X is Br, Cl or $HSO_4$ $R_1$: is linear alkyl chain from an saturated fatty acid, or hydroxyacid from 8 to 14 atoms of carbon bonded to the α-amino acid group through amidic bond. $R_2$ is a linear or branched alkyl chain from 1 to 18 carbon atoms or aromatic. R3: is Formula (II), where n can be from 0 to 4, and at least one antimicrobial agent characterised for its enhanced activity.

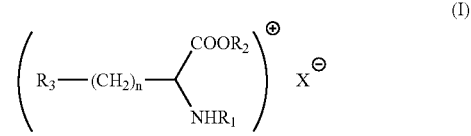

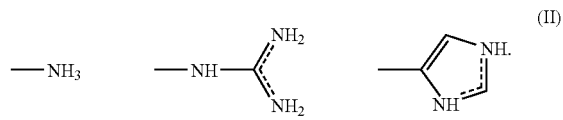

13 Claims, No Drawings

USE OF CATIONIC SURFACTANT AS ACTIVITY ENHANCER IN DEODORANTS AND ORAL CARE

This application is a national phase of International Application No. PCT/EP01/13221 filed Nov. 15, 2001 and published in the English language.

DESCRIPTION

This invention relates to a novel use of cationic surfactants as activity enhacers of the traditional antimicrobials and preparations according to this novel use in deodorants and oral care.

Many antimicrobials are known to be effective against specific and general bacteria which are present in the oral cavity and such bacteria which are responsible for the body odour. But, most of them display incompatibilities with the human skin and the mouth cavity mucous membranes, such as irritations and allergies and are toxic to human beings as well.

On the other hand, it has been demonstrated that cationic surfactants derived from lauric acid and arginine are biologically active substances, in particular, the ethyl ester of the lauramide of the arginine monohydrochloride, hereafter referred to as LAE. LAE has the chemical structure of formula (1), $$\left( \underset{NH_2}{\underset{\|}{H_2N}}\underset{}{\overset{NH}{\diagdown}}\underset{}{\diagup}\underset{}{\diagdown} \underset{NH}{\diagup}\underset{}{\diagdown} \underset{}{\overset{O}{\diagup}}\underset{}{\overset{O}{\diagdown}}\underset{}{\overset{}{\diagup}}\underset{}{\diagdown}(CH_2)_{10}-CH_3 \right)^{\oplus} Cl^{\ominus}$$

(1)

The preparation of this product has been described in a number of different patents.

Biological studies carried out at different research centres under supervision of the applicant of the present invention showed LAE acts mainly over the external and cytoplasmatic membrane of the microorganisms and, also, into the cytoplasmatic media, preventing their proliferation. Its action depends on the kind of microorganism and on the exposure time.

Besides, its metabolism in rats has been studied showing a fast absorption and metabolism into naturally-occurring amino acids and the fatty acid lauric acid, which are eventually excreted as carbon dioxide and urea. Toxicological studies have demonstrated LAE is completely harmless to animals and humans.

We have found that combinations of LAE with traditional antimicrobials have a better activity than LAE or these antimicrobials by themselves in the tested applications. This activity enhancement of LAE may be explained by its action over the cytoplasmatic membrane of the microorganisms.

So, it was the object of the present invention to provide further antimicrobial systems for cosmetic preparations for skin and oral care with in particular the goal of providing systems which comprise smaller amounts of the traditional antimicrobials in view of the risk of lack of tolerance.

The use of the invention relates to cationic surfactants derived from the condensation of fatty acids and esterified dibasic amino acids, according to the following formula:

$$\left( R_3-(CH_2)_n-\underset{NHR_1}{\overset{COOR_2}{\diagup}} \right)^{\oplus} X^{\ominus}$$

where:

$X^-$ is $Br^-$, $Cl^-$, or $HSO_4^-$ $R_1$: is a linear alkyl chain acyl group derived from an unsaturated fatty acid or hydroxyacid of from 8 to 14 atoms of carbon bonded to the α-amino acid group through the carbonyl.

$R_2$: is a linear or branched alkyl chain from 1 to 18 carbon atoms or an aromatic group.

$R_3$: is:

—$NH_3$

—$NH_3$     —$NH-\underset{NH_2}{\overset{NH_2}{\diagup\!\!\!\!\diagdown}}$     —$\underset{NH}{\overset{NH}{\diagup\!\!\!\!\diagdown}}$ and n can be from 0 to 4.

The most preferred compound of the above class of compounds is LAE.

This antimicrobial system is characterised for its enhanced activity. It has now been found that the antimicrobial activity of the combinations of LAE and the other compounds defined by the above formula (1) with most of the common antimicrobials used in formulations and preparations for skin and oral care is higher than the activity displayed by each of the components when used alone at the same dosage. There has been observed activity enhancement when the amounts of the compounds of formula (1) and the antimicrobial are reduced.

Thus, the adverse toxic effects and/or irritation and/or allergy displayed by the antimicrobial systems have also been reduced.

LAE can be used in association with common antimicrobials, such as 2,4,4'-trichloro-2'-hydroxy-diphenylether (triclosan), 3,4,4-trichlorocarbanilid (triclocarban), 2-phenoxyethanol, chlorhexidine salts, hexetidine and cetylpyridinium salts, for cosmetic formulations and preparations directed to avoid body odour and to provide oral care, which are applied to the epidermis or on the teeth and in the mouth cavity mucous membranes, in order to clean, perfume and/or change body odour and/or protect a good physical state.

The antimicrobial system of the invention comprises the cationic surfactant of formula (1) in an amount from 0.001 to 1% by weight and the concentration of the traditional antimicrobial agent from 0.0001% to 2% by weight relative to whole weight.

The antimicrobial system of the invention comprises more in particular a preferred amount of the traditional antimicrobial agent in deodorant applications, from 0.001 to 0.5% by weight of 2,4,4'-trichloro-2'-hydroxy-diphenylether (triclosan) and/or from 0.001 to 1.5% by weight of 3,4,4-trichlorocarbanilid (triclocarban) and/or from 0.001 to 1% by weight of 2-phenoxyethanol and/or 0.001 to 1% by weight of chlorhexidine salts.

The amount of the traditional antimicrobial agent in oral care applications is from 0.001 to 0.3% by weight of 2,4,4'-trichloro-2'-hydroxy-diphenylether (triclosan) and/or from 0.001 to 0.15% by weight of chlorhexidine gluconate and/or from 0.001 to 0.1% by weight of hexetidine and/or from 0.001 to 0.05% by weight of cetylpyridinium salts.

The composition of this invention comprises a medium which is compatible with the skin, the mucous membranes, and hair. These compositions may contain the usual components such as: fatty compounds such as mineral oil, animal oil, vegetal oil, from synthesis and silicon, and also alcohols, fatty acids and waxes; organic solvents, surface active agents, solubilizers and ionic and non ionic emulsifiers, thickening agents and jellying hydrophilic agents such as carboxyvinylic polymers (e.g. carbomer), acrylic copolymers (e.g. acrylates and alkylacrylates), polyacrylamides, polysaccharides, natural gums (e.g. xanthan gum); thickening agents and jellying lipophilic agents such as modified clays (ex. bentonite), fatty acid metallic salts, hydrophobic silica and polyethylene; perfumes and essential oils; astringents; antiperspirants; fluorides; humectants; sweeteners; softeners; excipients; antioxidants; sequestrant agents; opacifiers; filters; colouring compounds which are either hydrophilic or lipophilic, and pigments; and hydrophilic or lipophilic active ingredients. These compositions can also contain further antimicrobial agents which are different from the ones defined in the claims.

The amounts of these usual components mentioned in the previous paragraph are the normal ones as used in the art. These components are added to the antimicrobial systems of the invention without having any influence on their composition.

According to the invention the compositions can be in different cosmetic forms suitable for a topic application, such as:

a) Monophasic Systems:

water or hydro-glycolic solution that contains one or more surfactants to be used for the cleaning of the skin and mucous membranes;

water, hydro-alcoholic, hydro-glycolic or oily solution that can contain other additives to be used in the general care and/or protection for skin and/or mucous membranes;

water, hydro-alcoholic, hydro-glycolic or oily gel that can contain other additives to be used in general care and/or protection for skin and/or mucous membranes;

solid anhydride products that can contain other additives to be used in the general care and/or protection for skin and/or mucous membranes;

b) Biphasic Systems:

a water, hydro-alcoholic, hydro-glycolic or oily gel that can contain other additives to be used in general care and/or protection for skin and/or mucous membranes;

solid anhydride products that can contain other additives to be used in the general care and/or protection for skin and/or mucous membranes;

emulsions formed by dispersion of a oil phase in a water phase (O/W) or an inverse phase (W/O), to be used in general care and/or protection of the face skin and/or mucous membranes;

c) and combinations of the other systems that form multiphasic systems, suspensions and micro-emulsions.

The compositions previously mentioned can also be used as a spray, or as aerosol compositions and can contain a propulsion agent under pressure.

Thus, the compositions of the invention can have the aspect of a cream, a lotion, a milk, an emulsion, a gel, or an oil for the skin, a salt, a gel, a foam/spray or an oil for a bath and shower, and any other aspect to be shown.

The compositions according to the invention have been prepared according to usual techniques well known for an expert in the matter.

Procedure to Evaluate the Efficacy of the Antimicrobial System

The antimicrobial systems have been evaluated by the inhibition zone method (adapted from Association of Official Analytical Chemists, *J.Assoc.Off.Anal.Chem.*, 62, 466–467 (1982)), using specific test micro-organisms. These micro-organisms were:

for oral care products evaluation:

| Streptococcus mutans | ATCC | 25175 |
| Lactobacillus acidophilus | ATCC | 4355 |
| Staphylococcus aureus | ATCC | 6538 |
| Candida albicans | ATCC | 10231 | for deodorant products evaluation:

| Propionibacterium acnes | ATCC | 33179 |
| Corynebacterium sp. | ATCC | 6931 |
| Trichophyton Mentagrophytes | ATCC | 9533 |
| Staphylococcus epidermidis | ATCC | 12600 |

The method consits of measuring the inhibition zone created by the antimicrobial system of each cosmetic composition, placed in a a media hole, for every test micro-organism.

Each test micro-organism was inoculated into the appropriate culture media with a target concentration of approximately $10^6$ cfu/mL, and 20 mL of inoculated media was pipetted into petri dishes and let harden. It is also possible to seed the microorganism on the surface of the sterile media if that is suitable.

A hole of 15 mm diameter was made in the media and 0.5 mL of the cosmetic composition was deposited into the hold. It was allowed to diffuse for an hour and then incubated.

The temperature was kept at the optimum value for each micro-organism and dishes were protected against light.

Each test was carried out in triplicate.

The radius of the inhibition zone was measured at 24 hours for bacteria and 4 days for yeasts after the cosmetic composition was placed.

EXAMPLES

Different examples of cosmetic preparation formulations according to the invention have been assayed. The displayed examples are only a selection, and do not represent a restriction to the use of the antimicrobial system in other cases.

The concentrations of the antimicrobial agents used in the following examples are shown in Table 1:

TABLE 1

| Antimicrobial system | Composition |
|---|---|
| 1 | LAE at 0.3% |
| 2 | 2,4,4'-trichloro-2'-hydroxy-diphenylether (triclosan) at 0.2% |
| 3 | 3,4,4-trichlorocarbanilid (triclocarban) at 0.75% |
| 4 | 2-phenoxyethanol at 0.3% |
| 5 | chlorhexidine digluconate at 0.2% |
| 6 | hexetidine at 0.1% |

TABLE 1-continued

| Antimicrobial system | Composition |
|---|---|
| 7 | cetylpyridinium chloride at 0.04% |
| 8 | LAE at 0.05% with 2,4,4'-trichloro-2'-hydroxy-diphenylether (triclosan) at 0.1% |
| 9 | LAE at 0.05% with 3,4,4-trichlorocarbanilid (triclocarban) at 0.35% |
| 10 | LAE at 0.1% with 2-phenoxyethanol at 0.15% |
| 11 | LAE at 0.05% with chlorhexidine digluconate at 0.1% |
| 12 | LAE at 0.15% with hexetidine at 0.05% |
| 13 | LAE at 0.15% with cetylpyridinium chloride at 0.02% |

The activity of each antimicrobial system is related to the activity of antimicrobial system 1 through their inhibition radius. The resulting value is used to compare the activity of the traditional antimicrobial agent with and without LAE. So, a bigger value of this parameter represents a larger antimicrobial activity related to the 0.3% at LAE system.

Example of Mouth Rinse

Example 1

The composition of a direct use mouth rinse, made to test the effectiveness of the antimicrobial systems, is (in g):

| | |
|---|---|
| Ethanol | 9.00 |
| Glycerol | 10.00 |
| PEG 40 Hydrogenated castor oil | 2.00 |
| Sodium saccharinate | 0.15 |
| Aqua | 100 c.s.p. |

This formulation is completed with a suitable amount of the antimicrobial system of the invention and its antimicrobial activity is evaluated against formulations with traditional antimicrobial agents used alone.

The results are shown in the table 2.

TABLE 2

| Ant. sys. without LAE | | Ant. sys. with LAE | | | Ant. sys. without LAE | | Ant. sys. with LAE | |
|---|---|---|---|---|---|---|---|---|
| Ant. sys. Number ⇒ | Zone vs. ant. sys. 1 | Zone vs. ant. sys. 1 ⇐ | Ant. sys. Number | Ant. sys. Number ⇒ | Zone vs. system 1 | Zone vs. system 1 ⇐ | Ant. sys. Number |
| *Streptococcus mutans* | | | | | *Lactobacillus acidophilus* | | | |
| 2 ⇒ | 20 | 22 ⇐ | 8 | 2 ⇒ | 15 | 16 ⇐ | 8 |
| 5 ⇒ | 15 | 15 ⇐ | 11 | 5 ⇒ | 11 | 12 ⇐ | 11 |
| 6 ⇒ | 10 | 12 ⇐ | 12 | 6 ⇒ | 9 | 9 ⇐ | 12 |
| 7 ⇒ | 22 | 21 ⇐ | 13 | 7 ⇒ | 10 | 12 ⇐ | 13 |
| *Staphylococcus aureus* | | | | | *Candida albicans* | | | |
| 2 ⇒ | 18 | 19 ⇐ | 8 | 2 ⇒ | 8 | 10 ⇐ | 8 |
| 5 ⇒ | 12 | 13 ⇐ | 11 | 5 ⇒ | 7 | 6 ⇐ | 11 |
| 6 ⇒ | 9 | 9 ⇐ | 12 | 6 ⇒ | 8 | 8 ⇐ | 12 |
| 7 ⇒ | 15 | 17 ⇐ | 13 | 7 ⇒ | 9 | 10 ⇐ | 13 |

It is shown in the table 2 that the combination of LAE with the traditional antimicrobials leads to effects which are regularly higher than those displayed by these compounds used alone, with the advantages previously described.

Examples of Dentifrices

Example 2

The general composition of a standard opaque dentifrice, is (in g):

| | |
|---|---|
| Glycerol | 25.00 |
| Sodium saccharinate | 0.15 |
| EDTA 4 NA | 0.10 |
| Sodium monofluorophosphate | 1.00 |
| Silica | 5.00 |
| Sodium metaphosphate | 30.00 |
| Titanium dioxide | 0.20 |
| Hydroxyethylcellulose | 0.75 |

-continued

| | |
|---|---|
| Sodium lauryl sulfate | 0.80 |
| Aqua | 100 c.s.p. |

This formulation is completed with a suitable amount of the antimicrobial system of the invention and its antimicrobial activity is evaluated against formulations with traditional antimicrobial agents used alone.

The results are shown in the table 3.

TABLE 3

| Ant. sys. Number | ⇒ | Ant. sys. without LAE Zone vs. ant. sys. 1 | Ant. sys. with LAE Zone vs. ant. sys. 1 | ⇐ | Ant. sys. Number | Ant. sys. Number | ⇒ | Ant. sys. without LAE Zone vs. system 1 | Ant. sys. with LAE Zone vs. system 1 | ⇐ | Ant. sys. Number |
|---|---|---|---|---|---|---|---|---|---|---|---|
| *Streptococcus mutans* | | | | | | *Lactobacillus acidophilus* | | | | | |
| 2 | ⇒ | 15 | 17 | ⇐ | 8 | 2 | ⇒ | 10 | 10 | ⇐ | 8 |
| 5 | ⇒ | 12 | 14 | ⇐ | 11 | 5 | ⇒ | 8 | 9 | ⇐ | 11 |
| 6 | ⇒ | 7 | 10 | ⇐ | 12 | 6 | ⇒ | 9 | 8 | ⇐ | 12 |
| 7 | ⇒ | 12 | 13 | ⇐ | 13 | 7 | ⇒ | 11 | 12 | ⇐ | 13 |
| *Staphylococcus aureus* | | | | | | *Candida albicans* | | | | | |
| 2 | ⇒ | 13 | 14 | ⇐ | 8 | 2 | ⇒ | 8 | 8 | ⇐ | 8 |
| 5 | ⇒ | 9 | 10 | ⇐ | 11 | 5 | ⇒ | 7 | 7 | ⇐ | 11 |
| 6 | ⇒ | 7 | 8 | ⇐ | 12 | 6 | ⇒ | 6 | 7 | ⇐ | 12 |
| 7 | ⇒ | 9 | 12 | ⇐ | 13 | 7 | ⇒ | 9 | 9 | ⇐ | 13 |

It is shown in the table 3 that the combination of LAE with the common antimicrobials is equal or higher than those displayed by these compounds used alone, with the advantages previously described.

Further preparation examples of dentifrice, where the antimicrobial systems were also assayed, are described in the examples 3 to 5. The experimental rental results obtained in the example 2 are representative for these examples.

Example 3

The composition of a standard transparent dentifrice, is (in g):

| | |
|---|---|
| Glycerol | 19.00 |
| Sorbitol | 63.00 |
| Sodium saccharinate | 0.15 |
| EDTA 4 NA | 0.10 |
| Sodium fluoride | 0.20 |
| Silica | 15.00 |
| Hydroxyethylcellulose | 0.75 |
| Sodium lauryl sulfate | 0.80 |
| Aqua | 100 c.s.p. |

Example 4

The composition of a liquid dentifrice, is (in g):

| | |
|---|---|
| Glycerol | 5.00 |
| Sorbitol | 56.00 |
| Sodium saccharinate | 0.15 |
| EDTA 4 NA | 0.10 |
| Sodium fluoride | 0.20 |
| Silica | 16.00 |

-continued

| | |
|---|---|
| Hydroxyethylcellulose | 0.50 |
| Sodium lauryl sulfate | 0.80 |
| Aqua | 100 c.s.p. |

Example 5

The composition of a baking soda based dentifrice, is (in g):

| | |
|---|---|
| Glycerol | 10.00 |
| Sorbitol | 20.00 |
| Sodium saccharinate | 0.20 |
| EDTA 4 NA | 0.10 |
| Sodium monofluorophosphate | 1.00 |
| Silica | 15.00 |
| Sodium bicarbonate | 15.00 |
| Hydroxyethylcellulose | 0.50 |
| Sodium lauryl sulfate | 1.50 |
| Aqua | 100 c.s.p. |

Examples of Deodorants

Example 6

The general composition of a stick deodorant without alcohol, is (in g)

| | |
|---|---|
| Cyclomethicone | 25.00 |
| Stearyl alcohol | 26.00 |
| Octyl palmitate | 23.00 |
| Dioctyl adipate | 21.70 |
| C12–C15 alkyl benzoate | 2.00 |
| Glyceryl stearate | 2.00 |

This formulation is completed with a suitable amount of the antimicrobial system of the invention and its antimicrobial activity is evaluated against formulations with traditional antimicrobial agents used alone.

The results are shown in the Table 4.

TABLE 4

| Ant. sys. Number | ⇒ | Ant. sys. without LAE Zone vs. ant. sys. 1 | Ant. sys. with LAE Zone vs. ant. sys. 1 | ⇐ | Ant. sys. Number | Ant. sys. Number | ⇒ | Ant. sys. without LAE Zone vs. system 1 | Ant. sys. with LAE Zone vs. system 1 | ⇐ | Ant. sys. Number |
|---|---|---|---|---|---|---|---|---|---|---|---|
| *Propionibacterium acnes* | | | | | | *Corynebacterium* sp. | | | | | |
| 2 | ⇒ | 9 | 10 | ⇐ | 8 | 2 | ⇒ | 10 | 10 | ⇐ | 8 |
| 3 | ⇒ | 8 | 8 | ⇐ | 9 | 3 | ⇒ | 7 | 9 | ⇐ | 9 |
| 4 | ⇒ | 5 | 6 | ⇐ | 10 | 4 | ⇒ | 6 | 8 | ⇐ | 10 |
| 6 | ⇒ | 8 | 7 | ⇐ | 12 | 6 | ⇒ | 9 | 10 | ⇐ | 12 |
| *Trichophyton Mentagrophytes* | | | | | | *Staphylococcus epidermidis* | | | | | |
| 2 | ⇒ | 20 | 21 | ⇐ | 8 | 2 | ⇒ | 16 | 17 | ⇐ | 8 |
| 3 | ⇒ | 17 | 18 | ⇐ | 9 | 3 | ⇒ | 13 | 14 | ⇐ | 9 |
| 4 | ⇒ | 13 | 15 | ⇐ | 10 | 4 | ⇒ | 10 | 12 | ⇐ | 10 |
| 6 | ⇒ | 16 | 18 | ⇐ | 12 | 6 | ⇒ | 14 | 17 | ⇐ | 12 |

It is shown in the table 4 that the activity of a combination of LAE with the common antimicrobials is equal or higher than those displayed by these compounds used alone, with the advantages previously described.

Further examples of deodorants, where the antimicrobial systems were also assayed, are described in the following preparation examples 1 to 5. The experimental results obtained in the example 6 are representative for these preparation examples as well.

Preparation Example 1

The composition of a stick deodorant with alcohol, is (in g):

| | |
|---|---|
| Ethanol | 21.30 |
| Propylene glycol | 68.90 |
| Stearic acid | 6.10 |
| Octyl dodecanol | 1.00 |
| Sodium hydroxide | 0.93 |
| Aqua | 100 c.s.p. |

Preparation Example 2

The composition of a deodorant aerosol, is (in g):

| | |
|---|---|
| Ethanol | 51.93 |
| Isopropyl myristate | 1.50 |
| Propellant | 100 c.s.p. |

Preparation Example 3

The composition of a roll-on deodorant composition without alcohol, is (in g):

| | |
|---|---|
| CETEARETH-20 | 3.00 |
| Cetyl alcohol | 2.00 |
| Glyceryl stearate | 1.50 |
| Caprilic capric triglycerides | 2.00 |
| Isopropyl myristate | 2.00 |
| Aqua | 100 c.s.p. |

Preparation Example 4

The composition of a deodorant composition with alcohol for a roll-on, is (in g):

| | |
|---|---|
| Ethanol | 41.00 |
| Dipropylene glycol | 5.25 |
| Hydroxyethyl cellulose | 0.45 |
| Aqua | 100 c.s.p. |

Preparation Example 5

The composition of a deodorant cream, is (in g):

| | |
|---|---|
| Cetearyl alcohol + sodium cetearyl sulfate | 4.00 |
| CETEARETH-12 | 2.00 |
| Paraffinum | 4.00 |
| Propylene glycol | 3.00 |
| Caprilic capric triglycerides | 5.00 |
| Dimethicone | 1.00 |
| Isopropyl myristate | 5.00 |
| Aqua | 100 c.s.p. |

The invention claimed is:

1. An antimicrobial system which comprises:
   (a) a cationic surfactant, derived from the condensation of fatty acids and esterified dibasic amino acids, according to the following formula:

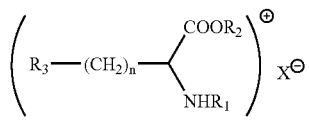

where:
   $X^-$ is $Br^-$, $Cl^-$, or $HSO_4^-$
   $R_1$: is a linear alkyl chain acyl group derived from an unsaturated fatty acid, or hydroxyacid of from 8 to 14 atoms of carbon bonded to the a-amino acid group through the carbonyl;
   $R_2$: is a linear or branched alkyl chain from 1 to 18 carbon atoms or aromatic.
   $R_3$: is:

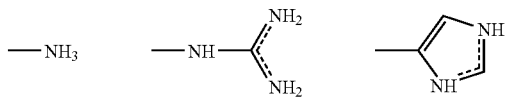

where n can be from 0 to 4, and
   (b) at least one antimicrobial agent;
   wherein said antimicrobial system is characterized for its enhanced antimicrobial activity.

2. The antimicrobial system as claimed in claim 1, wherein the cationic surfactant is the ethyl ester of the lauramide of arginine hydrochloride (LAE).

3. The antimicrobial system as claimed in claim 1, wherein the antimicrobial agent is selected from the group consisting of 2, 4,4'-trichloro-2'-hydroxy-diphenylether (triclosan) and/or 3,4,4-trichlorocarbanilid (triclocarban) and/or 2-phenoxyethanol and/or chlorhexidine salts and/or hexetidine and/or cetylpyridinium salts.

4. The antimicrobial system according to claim 1 wherein the concentration of the cationic surfactant is from 0.001 to 1% by weight and the concentration of the antimicrobial agent from 0.0001% to 2% by weight relative to the total weight of the antimicrobial system.

5. The antimicrobial system according to claim 4 wherein the amount of the antimicrobial agent in deodorant applications is from 0.001 to 0.5% by weight of 2,4,4'-trichloro-2'-hydroxy-diphenylether (triclosan) and/or from 0.001 to 1.5% by weight of 3,4,4-trichlorocarbaniid (triclocarban) and/or from 0.001 to 1% by weight of 2-phenoxyethanol and/or 0.001 to 1% by weight of chlorhexidine salts.

6. The antimicrobial system according to claim 4, wherein the amount of the antimicrobial agent in oral care applications is from 0.001 to 0.3% by weight of 2,4,4-trichloro-2'-hydroxy-diphenylether (triclosan) and/or from 0.001 to 0.15% by weight of chlorhexidine gluconate and/or from 0.001 to 0.1% by weight of hexetidine and/or from 0.001 to 0.05% by weight of cetylpyridinium salts in oral care applications.

7. The antimicrobial system according to claim 1, further containing fatty compounds; organic solvents, surface active agents, solubilizers and ionic and non-ionic emulsifiers, thickening agents and jellying hydrophilic agents; perfumes and essential oils; astringents; antiperspirants; fluorides; humectants sweeteners; softeners; excipients; antioxidants; sequestrant agents; opacifiers; filters; colouring compounds, pigments; and hydrophilic or lipophilic active ingredients.

8. A cosmetic and/or dermatological composition comprising the antimicrobial system of claim 1.

9. Cosmetic compositions for skin or oral care comprising the antimicrobial system of claim 4.

10. The composition according to claim 8 formed as an aqueous solution, hydro-alcoholic, hydro-glycolic emulsion, micro-emulsion, aqueous or an hydride gel of a vesicles dispersion.

11. A method for preventing body odor and/or providing oral care comprising applying to the skin and/or mouth cavity a cosmetic and/or dermatological composition containing the antimicrobial system according to claim 1.

12. A method for preventing proliferation of micro-organisms to avoid body odor and provide oral care by applying to the skin and/or mouth a cosmetic and/or dermatological composition containing the antimicrobial system according to claim 1.

13. The antimicrobial system according to claim 7, wherein the fatty compounds comprise a mineral oil, an animal oil, a vegetable oil, a synthetic oil, a silicon oil, alcohol, fatty acids or waxes; the thickening agents and jellying hydrophilic agents comprise carboxyvinylic polymers, acrylic copolymers, polyacrylamides, polysaccharides or natural gums; and the thickening agents and jellying lipophilic agents comprise modified clays, fatty acid metallic salts, hydrophobic silica, or polyethylene.

* * * * *